United States Patent
Cho et al.

(10) Patent No.: US 11,473,059 B2
(45) Date of Patent: Oct. 18, 2022

(54) METHOD FOR ENRICHMENT AND EXPANSION OF VIRUS ANTIGEN-SPECIFIC T CELLS

(71) Applicant: The Catholic University of Korea Industry-Academic Cooperation Foundation, Seoul (KR)

(72) Inventors: Seok Goo Cho, Seoul (KR); Nayoun Kim, Seoul (KR); Jung-Yeon Lim, Seoul (KR); Keon-Il Im, Seoul (KR); Young-Sun Nam, Seoul (KR)

(73) Assignee: LUCAS BIO CO. LTD.

( * ) Notice: Subject to any disclaimer, the term of this patent is extended or adjusted under 35 U.S.C. 154(b) by 0 days.

(21) Appl. No.: 15/769,872

(22) PCT Filed: Oct. 19, 2016

(86) PCT No.: PCT/KR2016/011751
§ 371 (c)(1),
(2) Date: Apr. 20, 2018

(87) PCT Pub. No.: WO2017/069512
PCT Pub. Date: Apr. 27, 2017

(65) Prior Publication Data
US 2018/0305665 A1    Oct. 25, 2018

(30) Foreign Application Priority Data

Oct. 22, 2015    (KR) .......................... 10-2015-0147584

(51) Int. Cl.
| | | |
|---|---|---|
| C12N 5/0783 | (2010.01) |
| A61K 39/235 | (2006.01) |
| C07K 16/28 | (2006.01) |
| A61K 39/12 | (2006.01) |
| A61K 35/17 | (2015.01) |
| C07K 16/24 | (2006.01) |
| A61K 39/00 | (2006.01) |

(52) U.S. Cl.
CPC ............ *C12N 5/0636* (2013.01); *A61K 35/17* (2013.01); *A61K 39/12* (2013.01); *A61K 39/235* (2013.01); *C07K 16/246* (2013.01); *C07K 16/28* (2013.01); *C12N 5/0646* (2013.01); *A61K 2039/5156* (2013.01); *A61K 2039/5158* (2013.01); *C12N 2501/2302* (2013.01); *C12N 2501/24* (2013.01); *C12N 2501/515* (2013.01); *C12N 2501/998* (2013.01); *C12N 2510/00* (2013.01); *C12N 2710/10011* (2013.01); *C12N 2710/16111* (2013.01); *C12N 2710/16134* (2013.01); *Y02A 50/30* (2018.01)

(58) Field of Classification Search
None
See application file for complete search history.

(56) References Cited

U.S. PATENT DOCUMENTS

| | | |
|---|---|---|
| 2008/0261307 A1 | 10/2008 | Kwon |
| 2015/0044258 A1 | 2/2015 | Knaus et al. |

FOREIGN PATENT DOCUMENTS

WO    2013/119947 A1    8/2013

OTHER PUBLICATIONS

Tsunoda et al. (Archive Jpn. Chir, Nov. 1991, p. 396-405).*
Munier et al. (Journal of Immunological Methods, 2009, p. 1-16).*
Lunemann et al. (JEM, 2008, vol. 205, p. 1763-1773).*
Schmidt-Wolf et al. (British Journal of Hematology, 1994, vol. 87, p. 453-458).*
V. Pfirrmann et al., "Cytomegalovirus-specific cytokine-induced killer cells: concurrent targeting of leukemia and cytomegalovirus," Cytotherapy 17:1139-1151, 2015.
A. Pievani et al., "Dual-functional capability of CD3$^+$30 CD56$^+$ CIK cells, a T-cell subset that acquires NK function and retains TCR-mediated specific cytotoxicity," Blood 118(12):3301-3310, Sep. 22, 2011.
Q. Zhang et al., "The dual-functional capability of cytokine-induced killer cells and application in tumor immunology," Human Immunology 76(5):385-391, Oct. 8, 2014.
Schmidt-Wolf et al., "Use of a SCID Mouse/Human Lymphoma model to Evaluate Cytokine-induced Killer Cells with Potent Antitumor cell Activity," J. Exp. Med., 174:139-149, 1991.

* cited by examiner

*Primary Examiner* — Agnieszka Boesen
(74) *Attorney, Agent, or Firm* — Leydig, Voit & Mayer, Ltd.

(57) ABSTRACT

The present invention relates to a method for inducing and proliferating target virus antigen-specific dual activated T cells, and can produce target virus antigen-specific dual activated T cells by treating monocytes, which are isolated from peripheral blood, with a cytokine and a virus antigen peptide mixture and culturing the same.

7 Claims, 6 Drawing Sheets

[Figure 1]
1. No peptivator
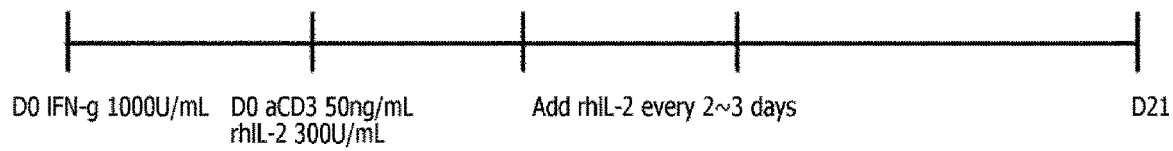
2. Single: With IFN-gamma stimulation
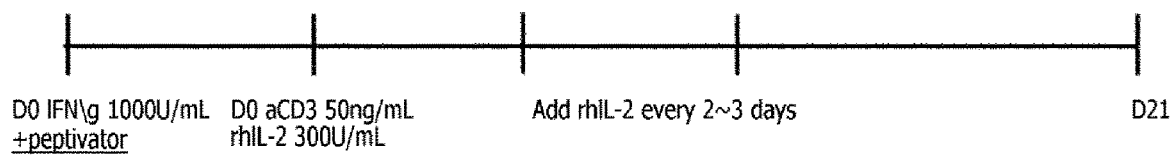
[Figure 2]
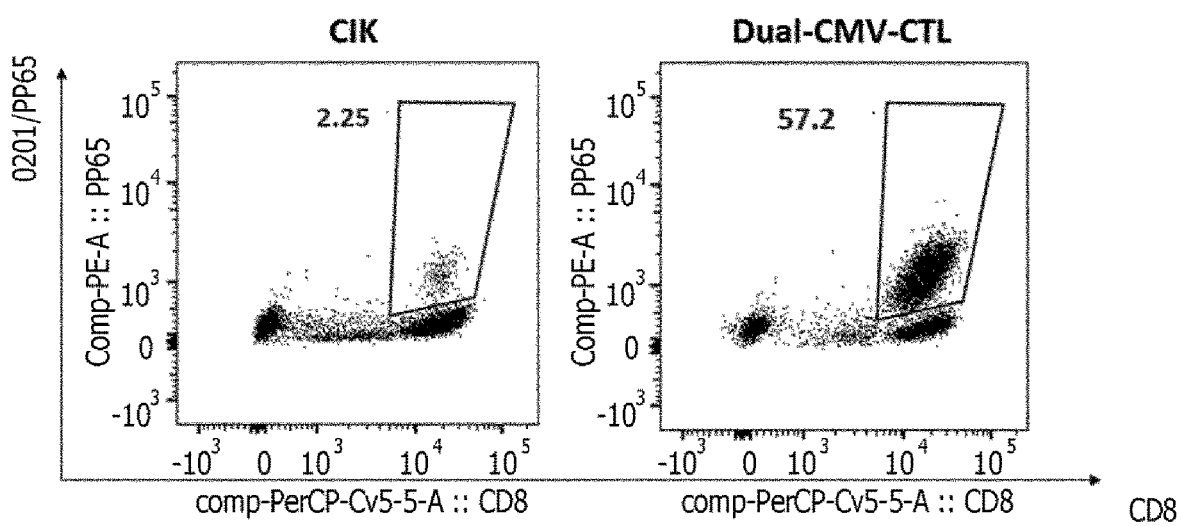

【Figure 3】
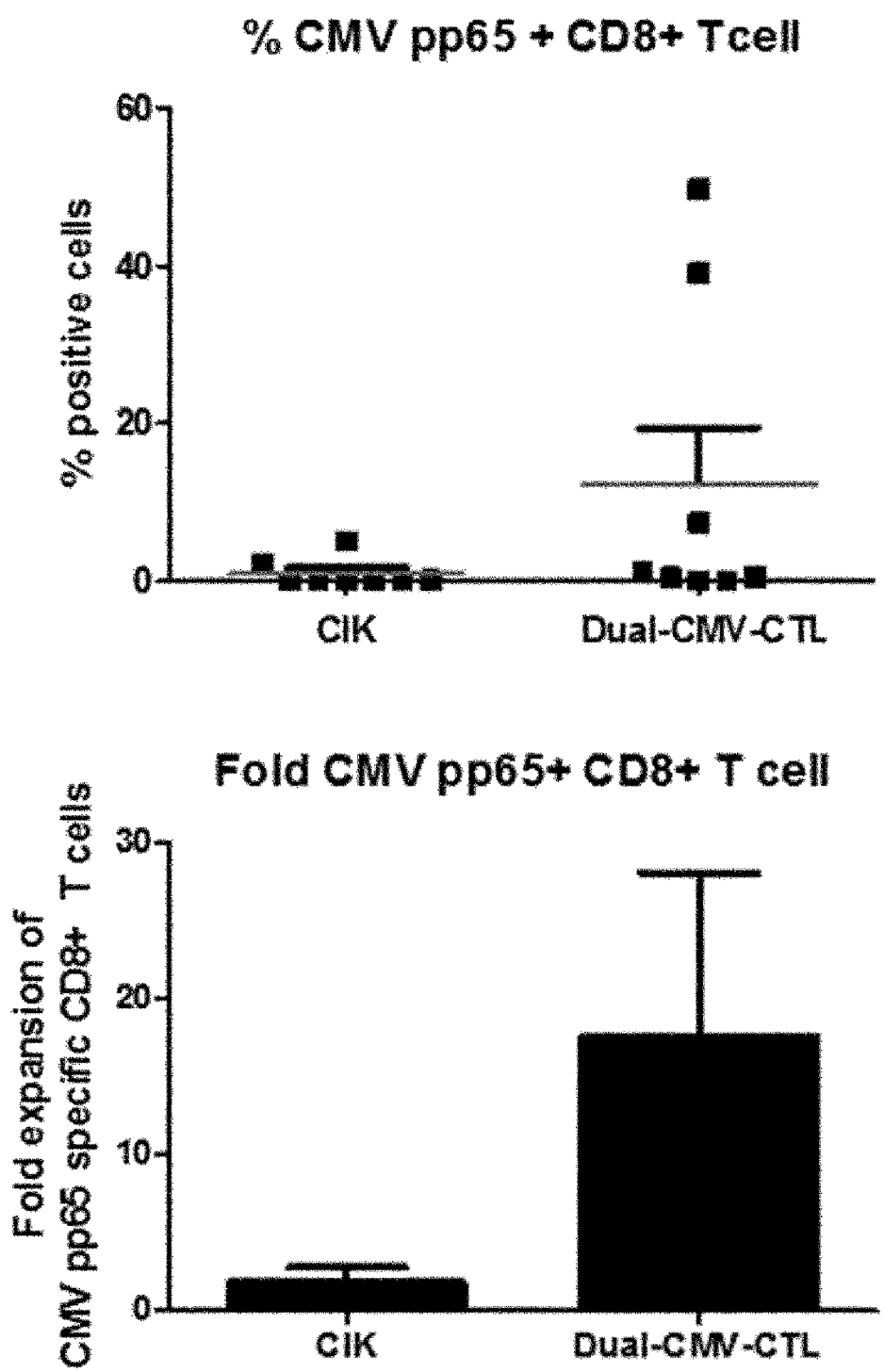

【Figure 4】
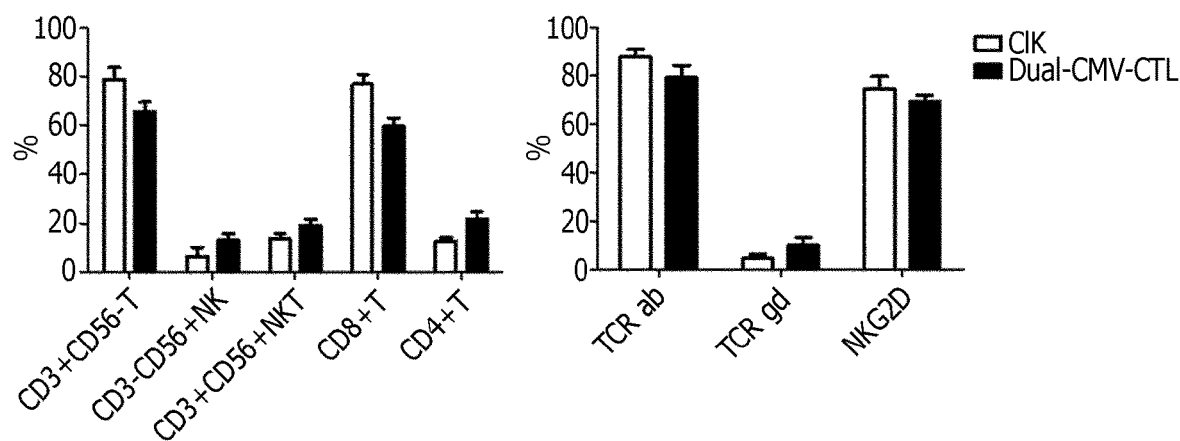
【Figure 5】
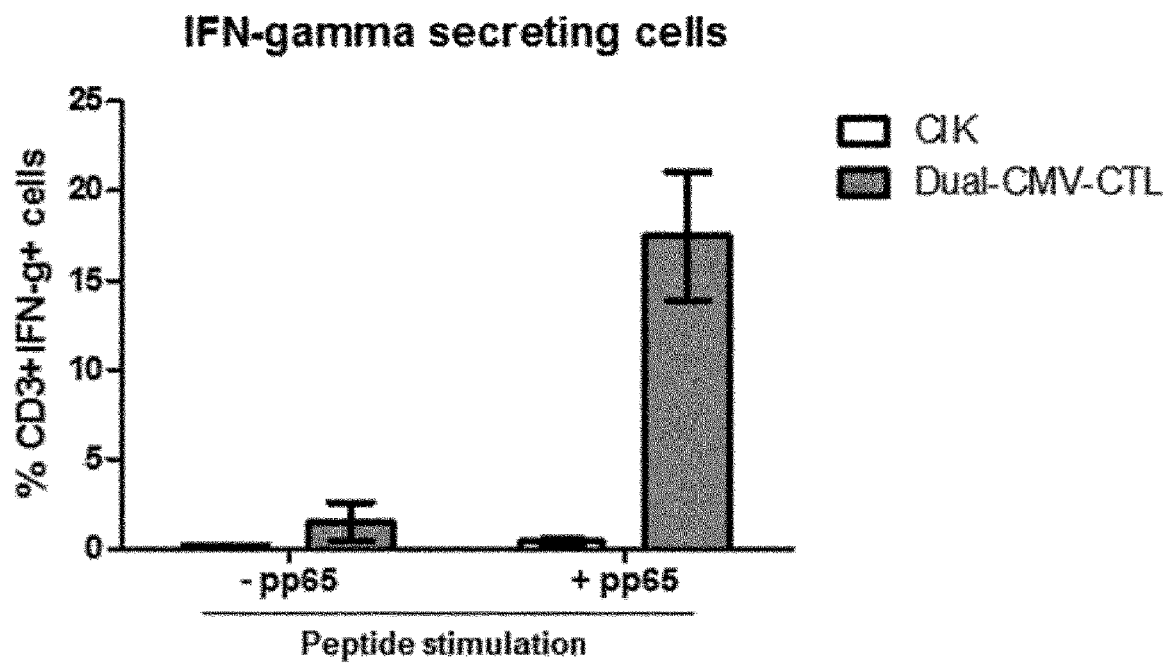

【Figure 6】
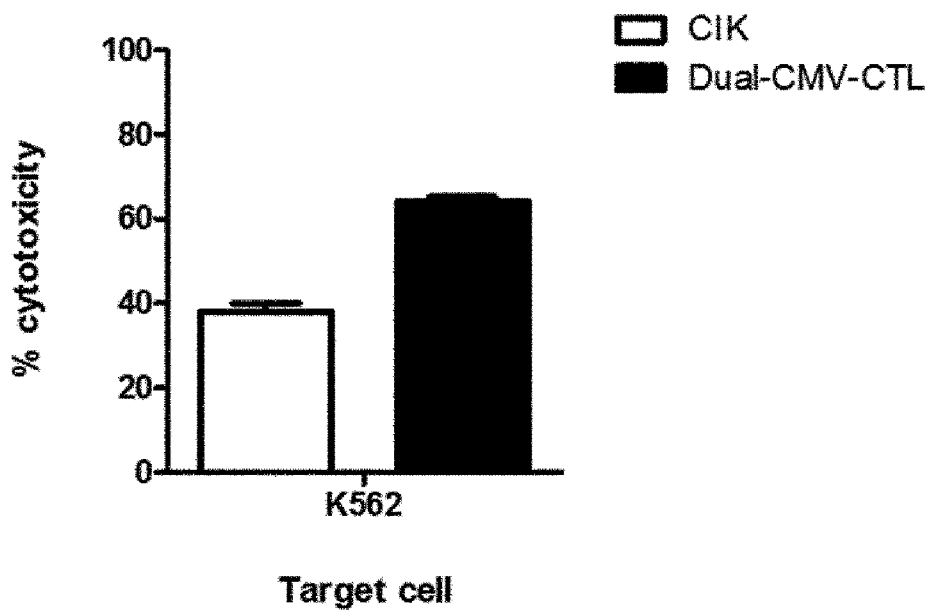
【Figure 7】
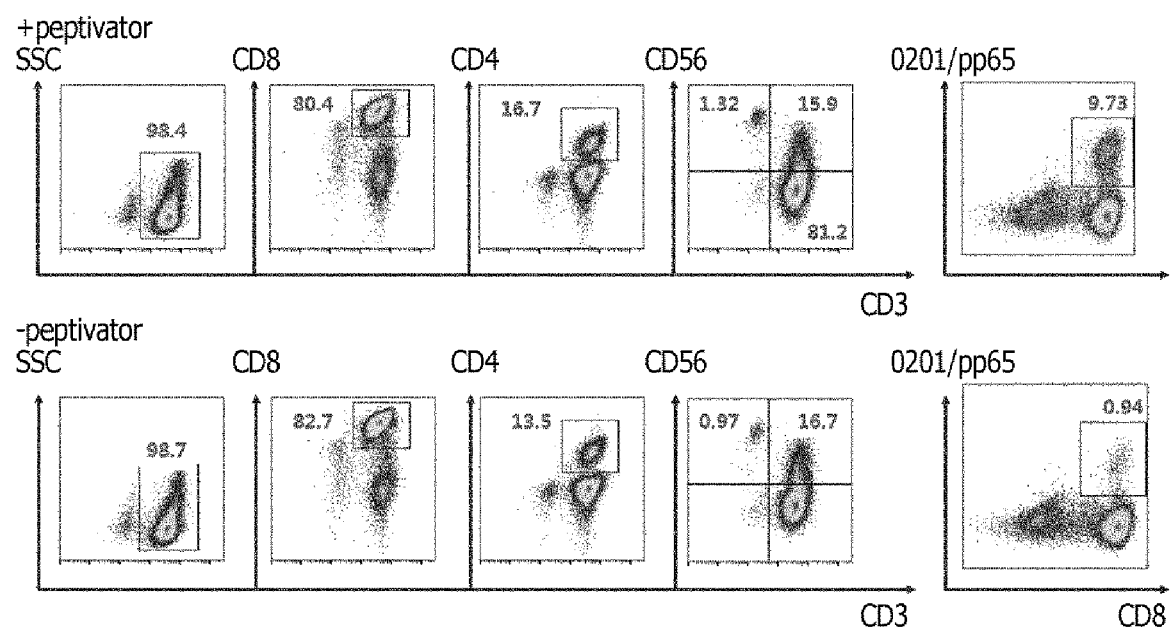

[Figure 8]
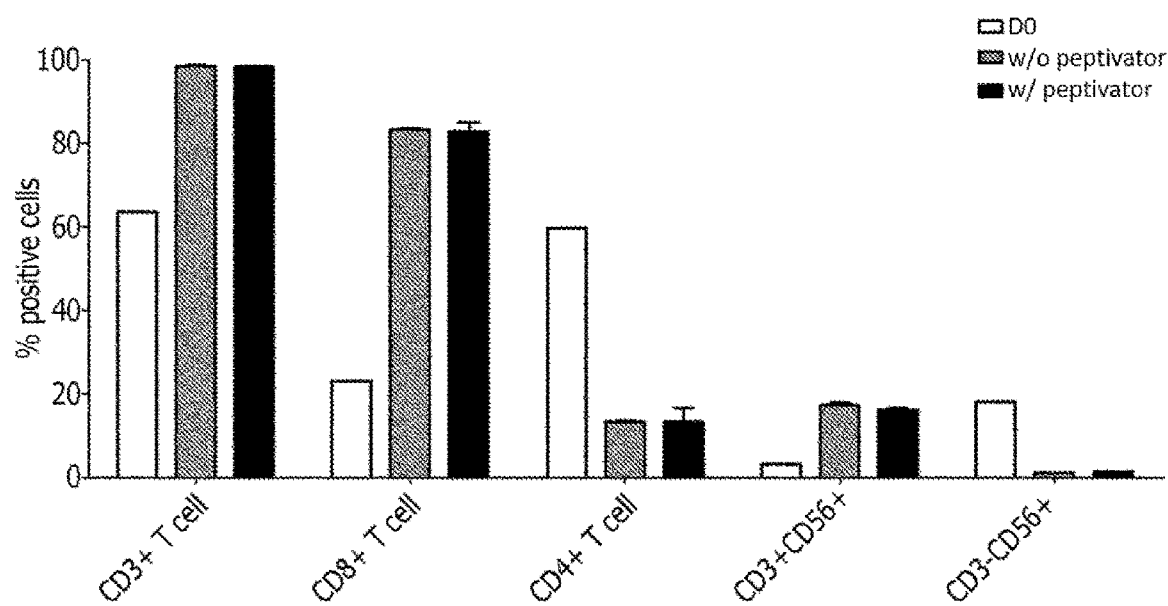

【Figure 9】
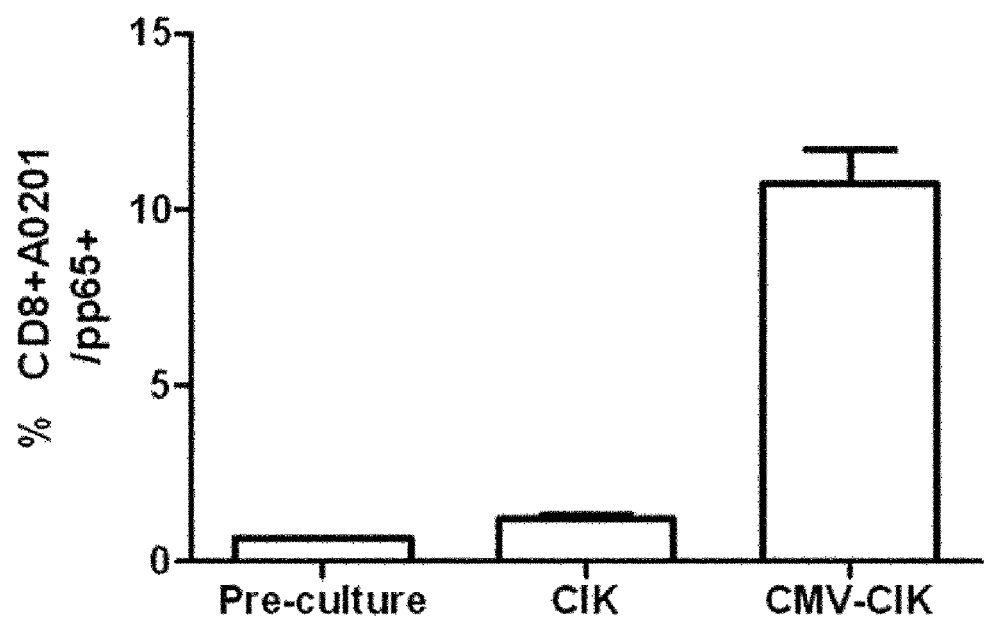
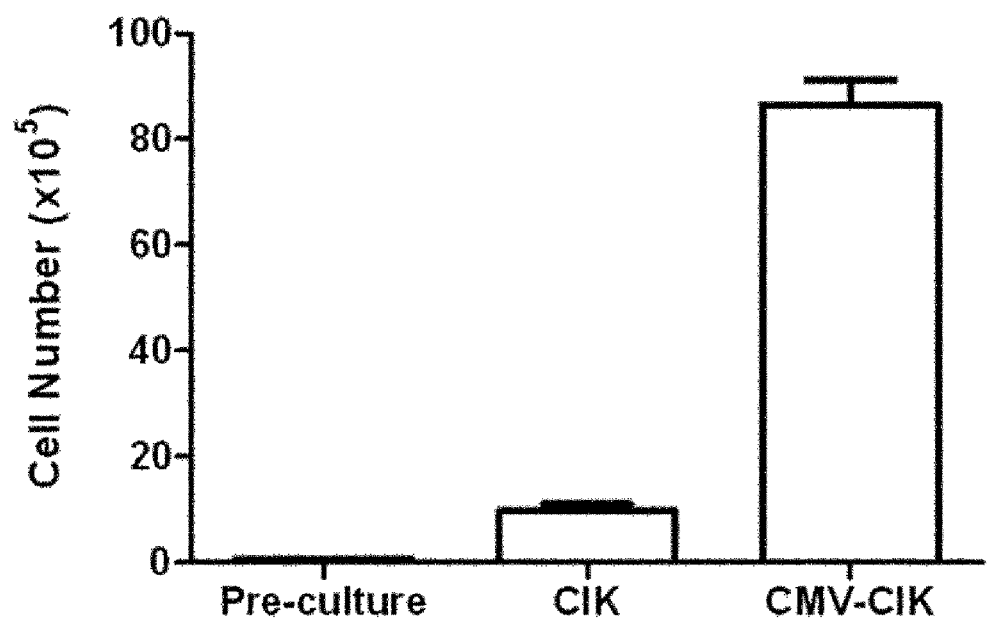

METHOD FOR ENRICHMENT AND EXPANSION OF VIRUS ANTIGEN-SPECIFIC T CELLS

CROSS-REFERENCE TO RELATED APPLICATIONS

This application is a U.S. National Stage Application filed under 35 U.S.C. § 371 of International Application No. PCT/KR2006/011751, filed Oct. 19, 2016, which claims the benefit of Korean Application No. KR 10-2015-0147584, filed Oct. 22, 2015. Both of these applications are hereby incorporated by reference in their entireties.

TECHNICAL FIELD

The present invention relates to a method for enriching and expanding virus antigen-specific T cells and a pharmaceutical composition for preventing and treating a virus-mediated disease including the same. This national research and development (R&D) project supporting the present invention is an innovative specialized R&D project led by the Korean Ministry of Health & Welfare entitled "Development of new drugs for treatment of immune and non-immune tissue damage based on low-molecular free radical scavengers (Research Project No.: HI14C3417)," which was supported by the Catholic University of Korea Industry-Academic Cooperation Foundation as the major organization.

BACKGROUND ART

Cytokine-induced killer cells (CIK cells) are immune cells in which a T cell marker 'CD3' and a natural killer cell (NK cell) marker 'CD56 molecule' are expressed at the same time. Because the cytokine-induced killer cells (hereinafter referred to as 'CIK cells') are derived from T cells so that the CIK cells have both characteristics and functions of NK cells, the CIK cells kill tumor cells regardless of major histocompatibility complexes (MHCs). Because the CIK cells induce cell death through binding of NKG2D receptors on the cell surface to NKG2D ligands expressed in tumor cells, this process is possible without dendritic cells presenting antigens unlike a general process of killing by T cells such as cytotoxic T lymphocytes (CTLs). Therefore, a method of amplifying and culturing CIK cells in vitro does not require co-culturing with other antigen-presenting cells (APCs), and has an easy production process because the CIK cells may be obtained through stimulation of cytokines. Also, because this method functions regardless of MHCs, it is known to eliminate various types of cancer cells, resulting in wide applicability. In Korea and abroad, it has been known that clinical trials are underway or completed for lymphoma, pancreatic cancer, hepatocellular carcinoma, myeloma, renal cell carcinoma, non-small cell lung cancer, gastric cancer, progressive pancreatic cancer, and the like. On the other hand, CTLs have a complicated production process because they require necessary processes for production and genetic variation of APCs, but have a very good anti-tumor effect when compared to the CIK cells because they induce a tumor-specific response in an MHC-dependent fashion. Also, the CTLs have drawbacks in that they have a high unit cost of production and exhibit relatively low safety and stability due to the genetic variation and the use of viruses, compared to the CIK cells.

The present inventors have established a new hypothesis for concomitantly imparting both of the function of non-specific NK cells such as CIK cells and the function of MHC-dependent antigen-specific CTLs when proper antigen presentation and activation signals are transmitted in a T cell activation process.

In the present invention, dual activated T cells are induced through treatment with a virus antigen peptide in the T cell activation process. As a result, it was confirmed that the virus antigen-specific T cells are measured in final cell products, compared to conventional methods of producing CIK cells. Also, it was confirmed that the virus antigen-specific T cells have an improved MHC-independent anti-tumor effect, compared to the conventional CIK cells. Based on these new results, the present inventors have strived to contribute to development of novel immunotherapeutic drugs by adding the function of MHC-dependent antiviral T cells as well as the MHC-independent anti-tumor effect.

DISCLOSURE

Technical Problem

The present invention is directed to providing virus antigen-specific T cells by treating peripheral blood mononuclear cells with a target virus antigen peptide mixture upon the culture of the peripheral blood mononuclear cells to produce T cells.

Technical Solution

To solve the above problems, one aspect of the present invention provides a method for enriching and expanding virus antigen-specific dual activated T cells, which includes treating peripheral blood mononuclear cells with IFN-γ and a virus antigen peptide mixture upon the culture of the peripheral blood mononuclear cells; and treating the peripheral blood mononuclear cells with IL-2.

To solve the above problems, another aspect of the present invention provides a pharmaceutical composition for preventing and treating a virus-mediated disease, which includes dual activated T cells prepared according to the method for inducing and proliferating dual activated T cells.

To solve the above problems, still another aspect of the present invention provides a kit for preparing virus antigen-specific dual activated T cells, which includes IFN-γ, IL-2, and a virus antigen peptide mixture.

To solve the above problems, yet another aspect of the present invention provides a method for inducing and proliferating virus antigen-specific cytokine-induced killer cells (CIK cells), which includes treating peripheral blood mononuclear cells with IFN-γ and a virus antigen peptide mixture upon the culture of the peripheral blood mononuclear cells; and treating the peripheral blood mononuclear cells with an anti-CD3 antibody and IL-2.

To solve the above problems, yet another aspect of the present invention provides a pharmaceutical composition for preventing and treating a virus-mediated disease, which includes cytokine-induced killer (CIK) cells prepared according to the method for inducing and proliferating cytokine-induced killer cells.

To solve the above problems, yet another aspect of the present invention provides a kit for preparing virus antigen-specific cytokine-induced killer cells, which includes IFN-γ, an anti-CD3 antibody, IL-2, and a virus antigen peptide mixture.

Advantageous Effects

The present invention is directed to methods for inducing and proliferating target virus antigen-specific dual activated T cells and CIK cells. In this case, the target virus antigen-specific dual activated T cells and the CIK cells can be produced by treating mononuclear cells, which are isolated from peripheral blood, with cytokines and a virus antigen peptide mixture together and culturing the mononuclear cells.

DESCRIPTION OF DRAWINGS

FIG. 1 shows a process of culturing CMV antigen-specific CIK cells.

FIG. 2 shows the results of measuring the number of CMV antigen-specific dual activated T cells using flow cytometry.

FIG. 3 shows the results of measuring the CMV antigen-specific dual activated T cells using a pentamer assay.

FIG. 4 shows the results of comparing phenotypes of the dual activated T cells after the dual activated T cells are cultured for 21 days.

FIG. 5 shows the results of measuring an IFN-γ secretion rate in the dual activated T cells and CIK cells after the dual activated T cells and CIK cells are stimulated with a CMV antigen peptide.

FIG. 6 shows a killing effect of the dual activated T cells on tumor cells.

FIG. 7 shows the results of measuring the number of the CMV antigen-specific CIK cells using flow cytometry.

FIG. 8 shows the results of comparing phenotypes of the CIK cells after the CIK cells are cultured for 21 days.

FIG. 9 shows the results of measuring the CMV antigen-specific CIK cells using a pentamer assay.

BEST MODE

Hereinafter, the configurations of the present invention will be described in detail.

The present invention provides a method for inducing and proliferating virus antigen-specific dual activated T cells, which includes treating peripheral blood mononuclear cells with IFN-γ and a virus antigen peptide mixture upon the culture of the peripheral blood mononuclear cells; and treating the peripheral blood mononuclear cells with IL-2.

In the present invention, the term "virus antigen-specific dual activated T cells" refers to T cells that are treated with a virus antigen peptide mixture upon the culture of the T cells to exhibit target virus antigen-specific characteristics, wherein the T cells exhibit both an MHC-independent anti-tumor effect and the function of MHC-dependent anti-viral T cells. The dual activated T cells according to the present invention include CD3+ T cells and CD3+CD56+ NKT cells, but a high proportion of virus antigen-specific T cells are contained in the CD3+ T cells. Therefore, the dual activated T cells according to the present invention may exhibit an effect of preventing or treating a virus-mediated disease because the dual activated T cells have additional target virus antigen-specific characteristics in addition to this general function of the T cells.

In the present invention, the term "peripheral blood mononuclear cells (PBMCs)", "PBMCs" or "mononuclear cells" refers to mononuclear cells that are isolated from peripheral blood generally used for anticancer immunotherapy. The peripheral blood mononuclear cells may be obtained from blood drawn from a person using a known method such as Ficoll density-gradient centrifugation.

According to one exemplary embodiment of the present invention, the peripheral blood mononuclear cells may be obtained from a normal person or a patient. The peripheral blood mononuclear cells used in the present invention do not necessarily have to be autologous, and peripheral blood mononuclear cells derived from the same species may be used to induce and proliferate the virus antigen-specific dual activated T cells according to the present invention.

The dual activated T cells according to the present invention are induced and proliferated by treating peripheral blood mononuclear cells with cytokines and a virus antigen peptide mixture upon the culture of the peripheral blood mononuclear cells.

In the present invention, the term "virus antigen" refers to an antigen protein such as a membrane protein or partial peptides thereof that causes a disease in a target subject to be treated by transplanting the dual activated T cells. For example, the virus antigen may be an antigen of a human latent virus such as a cytomegalovirus (CMV), Epstein-Barr virus (EBV), an adenovirus (ADV), BK virus (BKV), and the like.

In the present invention, peptides of the "peptide mixture" refer to peptides that constitute a viral protein which functions as an antigen and have a length of 10 to 20 amino acids. Therefore, the term "peptide mixture" refers to a mixture of the peptides.

In the present invention, the treating of the peripheral blood mononuclear cells with the IFN-γ and the virus antigen peptide mixture upon the culture of the peripheral blood mononuclear cells may further include isolating the mononuclear cells from a person's peripheral blood.

The treating of the peripheral blood mononuclear cells with the IFN-γ and the virus antigen peptide mixture upon the culture of the peripheral blood mononuclear cells may be carried out on day 0 of the culture, but the present invention is not limited thereto.

In the present invention, the treating of the peripheral blood mononuclear cells with the IL-2 may be carried out on day 4 of the culture. Specific culture conditions such as a treatment time of the cytokines, a certain temperature, and the like may vary depending on the type of virus antigens.

In the present invention, the term "cytokine" refers to an immunostimulatory cytokine that may be used to induce the peripheral blood mononuclear cells into cytokine-derived killer cells. In the present invention, IL-2 and IFN-γ are used as such cytokines.

The IFN-γ may be used at a concentration of 500 U/mL to 1,000 U/mL, for example, a concentration of 800 U/mL to 1000 U/mL, and the IL-2 may be used at a concentration of 200 U/mL to 1,000 U/mL, for example, a concentration of 200 U/mL to 800 U/mL.

When the peripheral blood mononuclear cells are treated with the cytokines and the target virus antigen peptide and cultured according to the present invention, the target virus-specific dual activated T cells may be obtained. The dual activated T cells thus obtained may be treated to treat a virus-mediated disease or a cancer.

The virus-mediated disease may include diseases caused by viral infections or virus-induced cancers. The diseases caused by the viral infections are, for example, found in immunocompromised patients whose immune system is damaged through graft engineering when there are mismatches between human leukocyte antigens (HLAs), and may include diseases mediated by human latent viruses, such as a cytomegalovirus (CMV), Epstein-Barr virus (EBV), an adenovirus (ADV), BK virus (BKV), and the like. The virus-induced cancers may, for example, include EBV-induced Burkitt's lymphoma, post-transplant lymphoproliferative disease (PTLD), Hodgkin's lymphoma, NK/T cell lymphoma, diffuse large B-cell lymphoma (DLBCL), primary effusion lymphoma, and the like, but the present invention is not limited thereto.

In the present invention, as a medium that may be used to culture the peripheral blood mononuclear cells any conventional medium used to induce and proliferate the peripheral blood mononuclear cells into T cells may be used without limitation. Media such as RPMI, DMEM, X-Vivo10, X-Vivo20, Cellgro SCGM, and the like may, for example, be used as such a medium. In addition, the culture conditions such as a temperature, and the like may follow conventional culture conditions for peripheral blood mononuclear cells.

The induction and proliferation of antigen-specific peripheral blood mononuclear cell-derived dual activated T cells according to the present invention may be carried out for 10 to 30 days, for example, 10 days to 25 days, 12 days to 25 days, 12 days to 21 days, 15 days to 21 days, 18 days to 21 days, or 20 days to 21 days.

According to one exemplary embodiment, the method may include treating CMV antigen-specific dual activated T cells with IFN-γ and a peptide mixture on day 0 of the culture upon the culture of the CMV antigen-specific dual activated T cells, treating the CMV antigen-specific dual activated T cells with IL-2 on day 4 of the culture, and treating the CMV antigen-specific dual activated T cells with IL-2 every 2 to 3 days for 21 days.

The present invention also provides a pharmaceutical composition including the antigen-specific dual activated T cells obtained according to the method.

In the following examples, CMV-pp65 antigen-specific T cells were measured for groups (examples) in which the mononuclear cells were cultured with a peptide mixture in the presence of IL-2, and groups (comparative examples) in which the mononuclear cells were cultured without a peptide mixture in the presence of IL-2. As a result, it was confirmed that the CMV-pp65 antigen-specific T cells were amplified only in the experimental groups in which the mononuclear cells were treated with the peptide mixture (FIG. 2).

Therefore, the virus antigen-specific dual activated T cells obtained according to the method of the present invention may be effectively used for prevention and treatment of a virus-mediated disease.

Specifically, the virus-mediated disease may include diseases caused by EBV, such as post-transplant lymphoproliferative disease (PTLD), Burkitt's lymphoma, Hodgkin's lymphoma, NK/T cell lymphoma, diffuse large B-cell lymphoma (DLBCL), primary effusion lymphoma, and the like; include diseases caused by CMVs, such as pneumonia, retinitis, enteritis, myelosuppression, and the like; include diseases caused by ADVs, such as cystitis, pneumonia, hepatitis, and the like; and include diseases caused by BKV, such as renal dysfunction, hemorrhagic cystitis, and the like, but the present invention is not limited thereto.

In the present invention, the subject may be a human in need of prevention and/or treatment of the virus-mediated disease. The subject may include patients or normal persons as well.

The pharmaceutical composition including the dual activated T cells according to the present invention may be formulated into a form in which the dual activated T cells are suspended at a proper concentration in an aqueous solution (for example, a phosphate buffer solution, an aqueous solution for conventional injections, and the like) containing proper ingredients, as necessary.

The pharmaceutical composition according to the present invention may be administered in conventional ways through routes of intravenous, intraarterial, intraperitoneal, intramuscular, intrasternal administration, and the like.

An effective amount of the dual activated T cells included in the pharmaceutical composition of the present invention refers to an amount required to achieve an effect of preventing or treating a virus-mediated disease. Therefore, the effective amount may be adjusted according to various factors including the type of a disease, the severity of a disease, the types and contents of other components included in the composition, and the age, weight, general health conditions, gender and diet of a patient, an administration time, a route of administration, a treatment period, drugs to be used in combination, and the like. For example, when administered once to several times a day, the CIK cells of the present invention may be administered, in the case of adults, at a dose of $1 \times 10^6$ cells/kg to $1 \times 10^{11}$ cells/kg, for example, a dose of $1 \times 10^6$ cells/kg to $1 \times 10^8$ cells/kg, but the present invention is not limited thereto.

Accordingly, the present invention provides a method for treating a virus-mediated disease, which includes administering the virus antigen-specific dual activated T cells to a subject in need thereof.

Also, the present invention provides a kit for preparing the virus antigen-specific dual activated T cells, which includes IFN-γ, IL-2, and a virus antigen peptide mixture.

According to the present invention, because a large amount of the dual activated T cells are induced and proliferated from a small amount of the peripheral blood mononuclear cells without using expensive equipment or various expensive cytokines, the efficiency and effectiveness of prevention and treatment of the virus-mediated disease using the dual activated T cells may be remarkably enhanced.

Also, the present invention provides a method for inducing and proliferating virus antigen-specific cytokine-induced killer cells (CIK cells), which includes treating peripheral blood mononuclear cells with IFN-γ and a virus antigen peptide mixture upon the culture of the peripheral blood mononuclear cells; and treating the peripheral blood mononuclear cells with an anti-CD3 antibody and IL-2.

In the method for inducing and proliferating CIK cells, all the contents disclosed in the method for inducing and proliferating dual activated T cells may be equally applied to the peripheral blood mononuclear cells, the virus antigen, the peptide mixture, the cytokines, the concentrations of the cytokines, and the culture medium for the peripheral blood mononuclear cells.

In the present invention, the term "virus antigen-specific cytokine-induced killer cells" refers to cells that are obtained by further treating the aforementioned dual activated T cells with an anti-CD3 antibody along with the IFN-γ, the virus antigen peptide mixture and the IL-2 to induce and proliferate the dual activated T cells.

In the present invention, the treating of the peripheral blood mononuclear cells with the IFN-γ and the virus antigen peptide mixture upon the culture of the peripheral blood mononuclear cells may be carried out on day 0 of the culture, but the present invention is not limited thereto.

In the present invention, the treating of the peripheral blood mononuclear cells with the anti-CD3 antibody and IL-2 may be carried out on day 1 of the culture. Specific culture conditions such as a treatment time of the cytokines and the anti-CD3 antibody, a temperature, and the like may vary depending on the type of virus antigens.

The IFN-γ may be used at a concentration of 500 U/mL to 1,000 U/mL, for example, a concentration of 800 U/mL to 1000 U/mL, and the IL-2 may be used at a concentration of 200 U/mL to 1,000 U/mL, for example, a concentration of 200 U/mL to 800 U/mL.

In the present invention, the "anti-CD3 antibody" refers to a protein that reacts specifically with CD3 antigens belonging to a group of molecules which are assembled with a T cell receptor (TCR) to form an antigen recognition complex, and the CD3 molecules have a longer intracellular area than TCR and play a role in transferring antigen recognition signals into the cells.

The anti-CD3 antibody may be used at a concentration of 30 ng/mL to 150 ng/mL, for example, a concentration of 50 ng/mL to 100 ng/mL.

When the peripheral blood mononuclear cells are treated with the cytokines and the target virus antigen peptide and cultured according to the present invention, the target virus-specific CIK cells may be obtained. The CIK cells thus obtained may be treated to treat a virus-mediated disease or a cancer.

The virus-mediated disease may include diseases caused by viral infections or virus-induced cancers. The diseases caused by the viral infections are found in immunocompromised patients whose immune system is damaged through graft engineering when there are mismatches between human leukocyte antigens (HLAs), and may, for example, include diseases mediated by human latent viruses, such as a cytomegalovirus (CMV), Epstein-Barr virus (EBV), an adenovirus (ADV), BK virus (BKV), and the like. The virus-induced cancers may, for example, include EBV-induced Burkitt's lymphoma, post-transplant lymphoproliferative disease (PTLD), Hodgkin's lymphoma, NK/T cell lymphoma, diffuse large B-cell lymphoma (DLBCL), primary effusion lymphoma, and the like, but the present invention is not limited thereto.

The induction and proliferation of the virus antigen-specific CIK cells according to the present invention may be carried out for 10 to 30 days, for example, 10 days to 25 days, 12 days to 25 days, 12 days to 21 days, 15 days to 21 days, 18 days to 21 days, or 20 days to 21 days.

According to one exemplary embodiment, the method may include treating CMV antigen-specific CIK cells with IFN-γ and a peptide mixture on day 0 of the culture upon the culture of the CMV antigen-specific CIK cells, treating the CMV antigen-specific CIK cells with an anti-CD3 antibody and IL-2 on day 1 of the culture, and treating the CMV antigen-specific CIK cells with IL-2 every 2 to 3 days for 21 days. The whole culture process for the CIK cells is shown in FIG. 1.

Also, the present invention provides a pharmaceutical composition including the virus antigen-specific CIK cells obtained according to the method.

According to one exemplary embodiment of the present invention, CMV-pp65 antigen-specific T cells were measured for groups (examples) in which the mononuclear cells were cultured with a peptide mixture in the presence of IL-2, and groups (comparative examples) in which the mononuclear cells were cultured without a peptide mixture in the presence of IL-2. As a result, it was confirmed that the CMV-pp65 antigen-specific T cells were amplified only in the experimental groups in which the mononuclear cells were treated with the peptide mixture (FIG. 7).

Therefore, the virus antigen-specific CIK cells obtained according to the method of the present invention may be used for prevention and treatment of a virus-mediated disease.

Specifically, the virus-mediated disease may include diseases caused by EBV, such as post-transplant lymphoproliferative disease (PTLD), Burkitt's lymphoma, Hodgkin's lymphoma, NK/T cell lymphoma, diffuse large B-cell lymphoma (DLBCL), primary effusion lymphoma, and the like; include diseases caused by CMVs, such as pneumonia, retinitis, enteritis, myelosuppression, and the like; include diseases caused by ADVs, such as cystitis, pneumonia, hepatitis, and the like; and include diseases caused by BKV, such as renal dysfunction, hemorrhagic cystitis, and the like, but the present invention is not limited thereto.

According to the present invention, the subject may be a human in need of prevention and/or treatment of the virus-mediated disease. The subject may include patients or normal persons as well.

The pharmaceutical composition including the CIK cells according to the present invention may be formulated into a form in which the CIK cells are suspended at a proper concentration in an aqueous solution (for example, a phosphate buffer solution, an aqueous solution for conventional injections, and the like) containing proper ingredients, as necessary.

The pharmaceutical composition according to the present invention may be administered in conventional ways through routes of intravenous, intraarterial, intraperitoneal, intramuscular, intrasternal administration, and the like.

An effective amount of the CIK cells included in the pharmaceutical composition of the present invention refers to an amount required to achieve an effect of preventing or treating a virus-mediated disease. Therefore, the effective amount may be adjusted according to various factors including the type of a disease, the severity of a disease, the types and contents of other components included in the composition, and the age, weight, general health conditions, gender and diet of a patient, an administration time, a route of administration, a treatment period, drugs to be used in combination, and the like. For example, when administered once to several times a day, the CIK cells of the present invention may be administered, in the case of adults, at a dose of $1\times10^6$ cells/kg to $1\times10^{11}$ cells/kg, for example, a dose of $1\times10^6$ cells/kg to $1\times10^8$ cells/kg, but the present invention is not limited thereto.

Accordingly, the present invention provides a method for treating a virus-mediated disease, which includes administering the virus antigen CIK cells to a subject in need thereof.

Also, the present invention provides a kit for preparing the virus antigen-specific cytokine-induced killer cells (CIK cells), which includes IFN-γ, an anti-CD3 antibody, IL-2, and a virus antigen peptide mixture.

According to the present invention, because a large amount of the CIK cells are induced and proliferated from a small amount of the peripheral blood mononuclear cells without using expensive equipment or various expensive cytokines, the efficiency and effectiveness of prevention and treatment of the virus-mediated disease using the CIK cells may be remarkably enhanced.

MODE FOR INVENTION

These and other advantages and features of the present invention and methods of achieving them will become apparent from the following description of preferred embodiments, with reference to the accompanying drawings. However, the present invention is not limited to the following examples but may be embodied in various forms. That is, these examples are provided so that the disclosure of the present invention will be through and complete, and the scope of the invention will be fully disclosed to those of ordinary skill in the art to which this invention belongs. This invention should be defined based on the scope of the appended claims.

Example 1: Preparation of CMV Antigen-Specific Dual Activated T Cells

Mononuclear cells were isolated from human peripheral blood by means of Ficoll density-gradient centrifugation, and then treated with 1,000 U/mL of an interferon gamma recombinant protein and 1 μg/mL of PepTivator (Miltenyi Biotec, Bergisch Gladbach, Germany) for cytomegalovirus (CMV) antigen pp65. After 4 days, the mononuclear cells were treated with 300 U/mL of an interleukin-2 (IL-2) recombinant protein, and cultured for 21 days to produce CMV antigen-specific dual activated T cells. IL-2 was added at a dose of 300 U/mL once every 2 to 3 days.

Comparative Example 1: Preparation of CIK Cells

Mononuclear cells were isolated from human peripheral blood by means of Ficoll density-gradient centrifugation, and then treated with 1,000 U/mL of an interferon gamma recombinant protein. After 24 hours, the mononuclear cells were treated with 50 ng/mL of an anti-CD3 antibody and 300 U/mL of an interleukin-2 (IL-2) recombinant protein, and cultured for 21 days to produce normal CIK cells. IL-2 was added at a dose of 300 U/mL once every 2 to 3 days.

Experimental Example 1: Measurement of CMV Antigen-Specific T Cells and NK Cells Surfaces of the dual activated T cells and the CIK cells were stained with fluorescence-conjugated antibodies against CD3 and CD8, which are T cell markers of the dual activated T cells and the CIK cell induced in the example and comparative example, and CD56, which is an NK cell marker, and then measured using flow cytometry. To measure the CMV antigen-specific dual activated T cells, the cell surfaces were stained with a fluorescent antibody bound to an antigen pp65/MHC complex, and measured using flow cytometry. In this case, the T cells binding to the pp65/MHC complex may be referred to as the CMV antigen pp65-specific dual activated T cells. The results of measurements using flow cytometry are shown in FIG. 2, and the results of measuring the CMV antigen-specific T cells using a pentamer assay are shown in FIG. 3.

As shown in FIGS. 2 and 3, it can be seen that a significantly high amount of the CMV-pp65 antigen-specific dual activated T cells was measured in the case of the experimental group in which the cells were treated with PepTivator, compared to the control in which the cells were not treated with PepTivator.

Experimental Example 2: Phenotypic Analysis of CMV-Specific Dual Activated T Cells The dual activated T cells and CIK cells produced in the example and comparative example were cultured, and the phenotypes of the cells were compared on day 21 of the culture. The results are shown in FIG. 4.

As shown in FIG. 4, it can be seen that the two types of the cells had similar phenotypes regardless of the addition of PepTivator for pp65. It can be seen that the dual activated T cells and CIK cells cultured for 21 days were all CD3-positive T cells, most of which were CD8-positive CTL cells, and approximately 15% of the final product had an NK/T cell phenotype in which CD3 and CD56 were expressed at the same time.

Experimental Example 3: Measurement of CMV-Specific IFN-Gamma Secretion Ability

The cells produced in the example and comparative example were collected, and stimulated with PepTivator for antigen pp65, and a level of IFN-gamma specifically secreted accordingly was then measured. The results are shown in FIG. 5.

As shown in FIG. 5, it can be seen that both the dual activated T cells and CIK cells did not secrete IFN-gamma when the cells were not treated with PepTivator, but a secretion rate of IFN-gamma in the dual activated T cells was remarkably increased when the cells were treated with PepTivator.

Experimental Example 4: Analysis of Killing Effect on Tumor Cells

The cells produced in the example and comparative example were collected, and co-cultured with chronic myeloid leukemia-derived K562 cells for 4 hours, and a killing effect on the K562 cells was then measured. The results are shown in FIG. 6.

As shown in FIG. 6, it can be seen that all the dual activated T cells and CIK cells had an MHC-independent killing effect on the K562 cells, and the dual activated T cells treated with the pp65 PepTivator during the culture process had an improved killing effect, compared to the CIK cells.

Example 2: Preparation of CMV Antigen-Specific CIK Cells

Mononuclear cells were isolated from human peripheral blood by means of Ficoll density-gradient centrifugation, and then treated with 1,000 U/mL of an interferon gamma recombinant protein and 1 μg/mL of PepTivator (Miltenyi Biotec, Bergisch Gladbach, Germany) for cytomegalovirus (CMV) antigen pp65. After 24 hours, the mononuclear cells were treated with 50 ng/mL of an anti-CD3 antibody and 300 U/mL of an interleukin-2 (IL-2) recombinant protein, and cultured for 21 days to produce CMV antigen-specific CIK cells. IL-2 was added at a dose of 300 U/mL once every 2 to 3 days. The culture process is schematically shown in FIG. 1.

Experimental Example 5: Measurement of CMV Antigen-Specific CIK Cells and NK Cells Surfaces of the CIK cells were stained with fluorescence-conjugated antibodies against CD3 and CD8, which are T cell markers of the CIK cells induced in Example 2 and Comparative Example 1, and CD56, which is an NK cell marker, and then measured using flow cytometry. To measure the CMV antigen-specific T cells, the cell surfaces were stained with a fluorescent antibody bound to an antigen pp65/MHC complex, and measured using flow cytometry. In this case, the T cells binding to the pp65/MHC complex may be referred to as the CMV antigen pp65-specific T cells. The results of measurements using flow cytometry are shown in FIG. 7.

As shown in FIG. 7, it can be seen that a significantly high amount of the CMV-pp65 antigen-specific T cells were measured in the case of the experimental group in which the cells were treated with PepTivator, compared to the control in which the cells were not treated with PepTivator.

Experimental Example 6: Phenotypic Analysis of CMV-Specific CIK Cells

The CIK cells produced in Example 2 and Comparative Example 1 were cultured, and the phenotypes of the CIK cells were compared on day 21 of the culture. The results are shown in FIG. 8.

As shown in FIG. 8, it can be seen that the CIK cells had similar phenotypes regardless of the addition of PepTivator for pp65. It can be seen that all the CIK cells cultured for 21 days were CD3-positive T cells, most of which were CD8-positive CTL cells, and approximately 15% of the final product had an NK/T cell phenotype in which CD3 and CD56 were expressed at the same time.

Experimental Example 7: Measurement of Antigen Pp65-Specific Cells of CMV-Specific CIK Cells The CIK cells produced in Example 2 and Comparative Example 1 were collected to measure the antigen pp65-specific T cells using a pentamer assay. The results are shown in FIG. 9.

As shown in FIG. 9, it was observed that a trace (0.1% or less) of CMV-specific T cells were present in peripheral blood prior to culturing. That is, it can be seen that such CMV-specific T cells were able to be amplified during the culture process. As shown in FIG. 9, it can be seen that there was little change in amplification of the CMV-specific T cells in the case of the control in which the T cells were not treated with the PepTivator, but the CMV-specific T cells were amplified approximately 9-fold in the experimental groups in which the T cells were treated with the PepTivator, compared to the control.

The invention claimed is:

1. A method for inducing and proliferating virus antigen-specific dual activated T cells comprising:
    culturing peripheral blood mononuclear cells under IFN-γ and a virus antigen peptide mixture for 4 days to selectively induce virus antigen-specific dual activated T cells; and
    proliferating the virus antigen-specific dual activated T cells under the presence of IL-2 and in the absence of anti-CD3 antibodies after the culturing step,
    wherein the proliferated virus antigen-specific dual activated T cells comprise CD3+CD8+CD56-cells and CD3+CD8+CD56+cells.

2. The method of claim 1, wherein the peripheral blood mononuclear cells are obtained from a normal person or a patient.

3. The method of claim 1, wherein the IFN-γ is used at a concentration of 500 U/mL to 1,000 U/mL.

4. The method of claim 1, wherein the IL-2 is used at a concentration of 200 U/mL to 1,000 U/mL.

5. The method of claim 1, wherein the induction and proliferation of the dual activated T cells is carried out for a total of 20 days or more.

6. The method of claim 5, wherein the induction and proliferation of the dual activated T cells is carried out for a total of 21 days.

7. The method of claim 1, wherein the virus antigen comprises antigens selected from the group consisting of a cytomegalovirus (CMV), Epstein-Barr virus (EBV), an adenovirus (ADV), and BK virus (BKV).

* * * * *